United States Patent
Eriksson et al.

(10) Patent No.: US 6,358,934 B1
(45) Date of Patent: Mar. 19, 2002

(54) ANTI-RETROVIRAL ACTIVITY OF 2',3'-DIDEOXY-3'-FLUORONUCLEOSIDES

(75) Inventors: Bertil Frank Harald Eriksson, Tumba; Karl Nils Gunnar Johansson, Enhörna; Göran Bertil Stening, Södertälje; Bo Fredrik Oberg, Uppsala, all of (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 07/319,840

(22) Filed: Mar. 7, 1989

Related U.S. Application Data

(63) Continuation of application No. 07/143,577, filed as application No. PCT/SE87/00316 on Jul. 2, 1987, now abandoned.

(30) Foreign Application Priority Data

Jul. 4, 1986 (SE) .............................................. 8602981

(51) Int. Cl.⁷ ............................................. A61K 31/70
(52) U.S. Cl. .............................. 514/45; 514/45; 514/46; 514/49; 514/50; 514/885
(58) Field of Search .............................. 514/45, 46, 49, 514/50, 885

(56) References Cited

U.S. PATENT DOCUMENTS

| 3,775,397 | A | * 11/1973 | Etzold et al. ................... 536/23 |
| 4,724,232 | A | 2/1988 | Rideout et al. |

FOREIGN PATENT DOCUMENTS

| DE | 0139793 | * 1/1980 | .................. 514/49 |
| DE | 158903 | | 2/1983 |
| DE | 0158903 | * | 2/1983 |
| DE | 209197 | | 4/1984 |
| DE | 0209197 | * | 4/1984 |
| EP | 0206497 | | 12/1986 |
| WO | 874929 | | 8/1987 |

OTHER PUBLICATIONS

Kowollik et al., "Ein Never Zugang Zu 1–(2, 3–Dideoxy–3–Fluor B–D–ribofurinosyl)–pyrimidinen," J. Fur. praktische Chemie, vol. 315, No. 5 895–900 (1973).*
Bikbulatov et al., the Chemical Abstracts, 84:25 824 u (1976).*
Cheng et al., "Human Immunodeficiency Virus Reverse Transcriptase," J. Biol Chem., 262 (5) pp 2187–2189 (1987).*
Herdewijn et al, the Chemical Abstracts, 107: 59403q (1987).*
Herdewijn et al, the Chemical Abstracts, 107: 176403a (1987).*
Mitsuya et al., "Protection of T Cells . . . In Vitro," *Retroviruses In Human Lymphoma/ Leukemia*, Japan Sci Soc. Press (1985) pp 277–288.*

Sandström et al., "Antiviral Therapy in AIDS" *Drugs* v. 34: 372–390 (1987) AIDS PRESS Limited.*
Herdewijn et al., J. Med. Chem. 30:1270–78 (1987).
Summers and Mason, cell, vol. 29:403–415 (1982).
Nordenfelt et al., J. Med. Virol. 22:231–36 (1987).
Vrang et al., Antimicrob. Agent and Chemother. vol. 29, No. 5, pp. 867–872 May 1986.
Langen et al., Acta Biol. Med. Germ., 29:483–494 (1972).
Langen et al., Acta Biol. Med. Germ., 23:759–266 (1969).
Langen et al., Proc. of the 6th Int'l Congress of Chemother. vol. II (1970).
Koshida et al., Inhibition of Human Immuodeficiency Virus in Vitro by combinations of 3'–Azido–3'–deoxythymidine (Zidovudine) and Phosphonoformate (Foscarnet). Antimicrob. Agents and Chemother. In press (1989).
Vrang et al., Reverse Transcriptase from HIV–1, HIV–2, and SIV are Susceptible to Inhibition by Foscarnet and 3'–azido–3'–deoxythymidine triphosphat.
Antimicrob. AGents and Chemother 32:1733–1734 (1988).
Bazin et al., An Analysis of the Inhibition of Replication of HIV and MuLV by Some 3'–blocked Pyrimidine Analogs, Biochem. Pharm. vol. 1989, No. 109–119.
Abstract No. 3007, Abstracts from Book 1, IV Int'l, Conference on AIDS, Stockholm, Jun. 12–16, 1988.
Putkonen et al, Journal of Acquired Immune Deficiency Syndromes, vol. 2, pp. 359–365 (1989).
Wu et al, Antimicrobial Agents and Chemotherapy, vol. 32, No. 12, pp. 1887–1890 (1988).
Oberg, Antiviral Therapy, IV Int'l. Conf. on AIDS, Stockholm 1988, J. Acquired Immune Deficiency Syndromes 1:257–266 (1988).
Lundgren et al., Inhibition of Early Occurence of Viral Antigen in SIV–Infected Macaques as a Measurement of Antiviral Efficacy (Manuscript 1989).
Wu et al., Antimicrob. Agent. and Chemother., vol. 32 No. 12, pp. 1887–1890 (Dec. 1988).

(List continued on next page.)

*Primary Examiner*—James O. Wilson
(74) *Attorney, Agent, or Firm*—Birch, Stewart, Kolasch & Birch, LLP

(57) ABSTRACT

Use of a compound of the formula

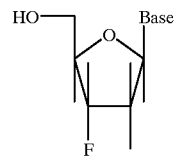

wherein Base is thymine, Cytosine, adenine or guanine, or a physiologically acceptable salt thereof, for therapeutic or prophylactic control or treatment of retrovirus infections, including HIV, and hepatitis B virus infections and to a method for such treatment, especially for AIDS.

21 Claims, No Drawings

OTHER PUBLICATIONS

Kowollik et al., "Ein neuer Zugang zu 1–(2', 3'–Didesoxy–3–fluor–B–D–ribo–furanosyl)–pyrimidinen", Journal fur praktische Chemie, vol. 315, No. 5: 895–900 (1973).

Chemical Abstracts, vol. 84, No. 25824u (1976), Bikbulativ et al., Vopr. Virusol. 1975, (5), 625–6 (Russ.).

Chemical Abstracts, vol. 102, No. 39565n (1985), Waqar et al., J. Cell. Physiol. 1984, 121 (2), 402–8 (Eng).

Langen et al., "5'–deoxy–5'–fluorothymidine and 3'–deoxy–3'–fluorothymidine Two Thymidine Analogues with Different Points of Attack at the Molecular Level", Progress in Antimicrobial and Anticancer Chemotherapy: Proceedings of the 6th International Congress of Chemotherapy, vol. II, pp. 394–397 (1970).

* cited by examiner

ANTI-RETROVIRAL ACTIVITY OF 2',3'-DIDEOXY-3'-FLUORONUCLEOSIDES

This application is a continuation of application Ser. No. 07/143,577, filed on Dec. 30, 1987, which is the national stage of PCT/SE87/00316, filed Jul. 2, 1987.

FIELD OF THE INVENTION

The present invention relates to the use of known chemical compounds and physiologically acceptable salts thereof for the therapeutic and prophylactic control and treatment of the Acquired Immuno Deficiency Syndrome (AIDS), infections by Human Immunodeficiency Virus, hepatitis B virus infections and retrovirus infections for such control and treatment in animals and man.

BACKGROUND OF THE INVENTION

In the late seventies a new disease was reported, which subsequently was referred to as Acquired Immuno Deficiency Syndrome (AIDS). It is now generally accepted that a retrovirus referred to as HIV (Human Immuno Deficiency Virus, formerly known as Human T-cell Lymphotropic Virus (HTLV-III) or Lymphadenopathy Associated Virus (LAV) plays an essential role in the etiology of AIDS.

AIDS is characterized by a profound immunodeficiency due to low numbers of lymphocyte-T-helper cells, which are the targets for HIV (also called HTLV-III/LAV) infection. The profound immunodeficiency in AIDS patients makes these patients highly susceptible to a variety of opportunistic infections of bacterial, fungal, protozoal or viral etiology. The etiological agents among viral opportunistic infections are often found in the herpes virus group, i.e., Herpes simplex virus (HSV), Varicella Zoster virus (VZV), Epstein-Barr virus (EBV) and, especially, cytomegalovirus (CMV). Other retroviruses affecting humans are HTLV-I and II and examples of retroviruses affecting animals are feline leukemia virus and equine infectios anaemia virus.

Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrhosis and liver tumours. In some cases the hepatitis infections also take a rapid and severe course as in fulminant B hepatitis with about 90% mortality. At present there is no known effective treatment against hepatitis B infections.

PRIOR ART

The compound 3'-deoxy-3'-fluoro-thymidine is described in Journal f. prakt. Chemie, Vol. 315, 895–900 (1973) as having cytostatic and virustatic activity as selective inhibitor of DNA synthesis. In the same article the synthesis of the compound 2',3'-dideoxy-3'-fluorocytidine is described.

The compounds 2',3'-dideoxy-3'-fluoroadenosine and 2',3'-dideoxy-3'-fluoroguanosine are described in the East-German patents DD 158903 and DD 209197, respectively, as virostatic agents.

DISCLOSURE OF THE INVENTION

It has been found according to the present invention that the compounds of the formula

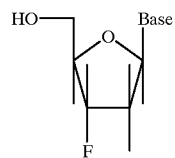

wherein Base is thymidine, cytosine, adenine or guanine, or a physiologically acceptable salt thereof, present a new possibility to block the multiplication of retrovirus, including HIV, and hepatitis B virus, respectively, by use a nucleoside analogue of said formula. Accordingly, the nucleoside analogues of said formula and physiologically acceptable salts thereof, have unobvious and beneficial properties as prophylactic and/or therapeutic agents in the control or treatment of retrovirus and hepatitis B virus infections, respectively. Said nucleosides are especially interesting as agent capable of inhibiting the activity of human immunodeficiency virus (HIV; HTLV-III/LAV virus) in animals and man.

All retrovirus, including (HIV, HTLV-III/LAV), require an enzyme called reverse transcriptase in their natural cycle of replication.

Hepatitis B virus (HBV) is a DNA virus with a unique circular double-stranded DNA genome which is partly single-stranded. It contains a specific DNA polymerase required for viral replication. This DNA polymerase also acts as a reverse transcriptase during the replication of HBV DNA via an RNA intermediate.

The compounds of the invention are transformed by cells/or enzymes to triphosphates which inhibit the reverse transcriptase of retrovirus including HIV as well as the activity of DNA polymerase of hepatitis B virus.

The following known compounds constitute part of the invention as prophylactic and therapeutic agents in control or treatment of retrovirus or hepatitis B virus infections:

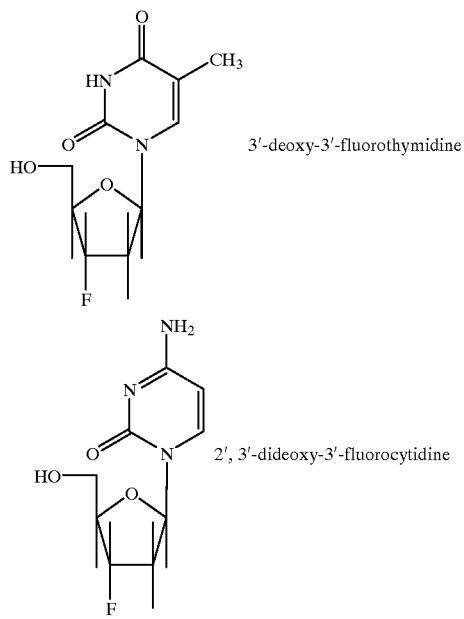

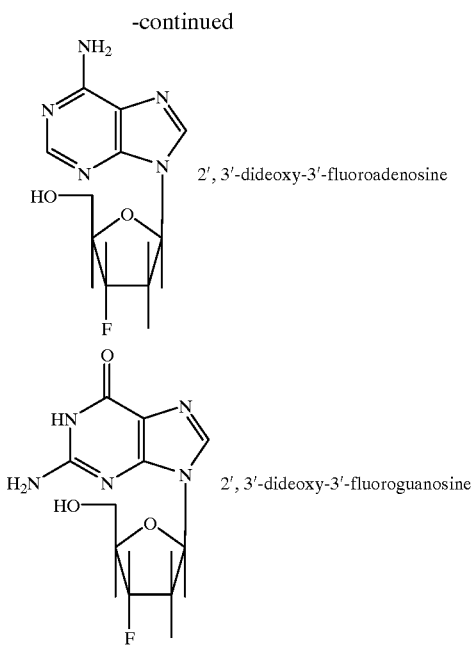

3'-Deoxy-3'-fluorothymidine is especially preferred as an agent for use in control or treatment of retrovirus, including HIV (HTLV-III/LAV) and hepatitis B virus infections in animal and man.

In clinical practice the nucleosides of the invention will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragées, capsules, granulates, suspensions, elixirs, syrups, solutions etc. Usually the active substance will comprise between 0.05 and 20% for preparations intended for injection and between 10 and 90% for preparations intended for oral administration.

In the treatment of patients suffering from retrovirus especially HIV or hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of patient etc., and may have to be individually adjusted. As a possible range for the amount of the compounds of the invention or a physiologically acceptable salt thereof be administered per day may be mentioned from about 10 mg to about 10 000 mg, preferentially 100–500 mg for intravenous administration and preferentially 100–1000 mg for oral administration.

Salts

The physiologically acceptable salts of the nucleosides of the invention are suitable acid addition salts, derived from non-toxic acids. Such acid addition salts include, for example, those derived from inorganic acids such as hydrochloric acid, hydroiodic acid, sulphuric acid, phosphoric acid and sulfamic acid, organic sulphonic acids such as p-toluenesulphonic acid, methanesulphonic acid, p-chlorobenzonesulphonic acid, ethanesulfonic acid, and benzenesulfonic acid and organic carboxylic acids such as maleic acid, malic acid, lactic acid, citric acid, tartaric acid, succinic acid, oxalic acid, acetic acid, isethionic acid, gluconic acid, pantothenic acid and lactobionic acid.

Experimental Tests

Test I. Effect of 3'-deoxy-3'-fluorothymidine as a triphosphate on the DNA polymerase of hepatitis B virus (HBV) in cell free assay Since hepatitis B virus cannot be grown in cell cultures, a cell-free assay system of the hepatitis B virus DNA polymerase has been used to investigate the effect of 3'-deoxy-3'-fluorothymidine. 3'-Deoxy-3'-fluorothymidine in cells is transformed to 3'-deoxy-3'-fluorothymidine-5'-triphosphate.

The HBV associated DNA polymerase activity can be measured in vitro (Kaplan et al., J. Virol., 12, 995–1005, 1973). A slight modification of this method has been used to test the substance for inhibition of this DNA polymerase activity. (Nordenfelt E., Öberg, B., Helgstrand E. and Miller E. Acta path., Microbiol. Scand. Sect B, 88:169–175, 1980). With this assay the 3'-deoxy-3'-fluorothymidine-5'-triphosphate has been tested, instead of the prodrug 3'-deoxy-3'-fluorothymidine, to evaluate its potential against hepatitis B virus DNA polymerase.

3'-deoxy-3'-fluorothymidine-5'-triphosphate was added to the final concentrations of 0.01 $\mu$M, 0.05 $\mu$M, 0.1 $\mu$M, 0.5 $\mu$M and 1.0 $\mu$M in the reaction mixture. The inhibition is calculated after 3 hours incubation at 37° C. and based on cpm compared to control with added water. The test result is shown in Table 1.

TABLE I

Inhibition of hepatitis B virus (HBV) DNA polymerase activity by 3'-deoxy-3'-fluorothymdine-5'-triphosphate

| Concentration of 3'-deoxy-3'-fluorothymidine-5'-triphosphate ($\mu$M) | % inhibition |
| --- | --- |
| 0.01 | 17 |
| 0.05 | 17 |
| 0.1 | 39 |
| 0.5 | 79 |
| 1 | 88 |

From the results shown in Table I the apparent $ID_{50}$-value of 3'-deoxy-3'-fluorothymidine was found to be 0.16 $\mu$M.

Test II. Effect of 3'-deoxy-3'-fluorothymidine as a triphosphate on the reverse transcriptase of HIV (HTLV-III/LAV) in cell free assay.

A cell-free assay system has been used to investigate the inhibition of 3'-deoxy-3'-fluorothymidine on reverse transcriptase of HIV (HTLV-III/LAV). The assay was performed as described by Vrang et Öberg, Antimicrob. Agents Chemother. 29, 867–872 (1986). With this assay the 3'-deoxy-3'-fluoro-thymidine-5'-triphosphate has been tested, instead of the prodrug 3'-deoxy-3'-fluorothymidine to evaluate its potential against reverse transcriptase from HIV (HTLV-III/LAV). The test result is shown in Table II.

TABLE II

Inhibition of HIV (HTLV-III/LAV) reverse transcriptase by 3'-deoxy-3'-fluorothymidine-5'-triphosphate

| Concentration of 5'-triphosphate 3'-deoxy-3'-fluorothymidine ($\mu$M) | % inhibition |
|---|---|
| 0.01 | 12 |
| 0.05 | 27 |
| 0.1 | 38 |

From the results in Table II, the $ID_{50}$-value of 3'-deoxy-3'-fluoro-thymidine with regard to the activity of HIV reverse transcriptase was found to be 0.2 $\mu$M by extrapolation.

Test III. Effect of 3'-deoxy-3'-fluorothymidine on HIV (HTLV-III/LAV) in H9 cells Material and Methods; HIV infection of H9 cells H9-cells ($2 \times 10^6$) were preincubated overnight with 3'-deoxy-3'-fluorothymidine at various concentrations. The cells were then pelleted and dispersed in 2.5 ml phosphate buffered saline (PBS) including 2 $\mu$g/ml Polybrene. After incubation for 30 min the cells were pelleted and infected with HIV. After an adsorption period of 1 hour the cells were pelleted and washed once with 2.5 ml PBS. To each culture 7 ml media including 3'-deoxy-3'-fluorothymidine at studied concentrations was added. Samples for reverse transcriptase activity tests were taken as indicated.

Assay 1.3 ml samples from the supernatant of each culture were centrifuged at 18 000 rpm in a 55-34 rotor for 1.5 hours and the virus pellet resuspended in 100 $\mu$l buffer containing 50 mM Tris-HCl, pH 7.5; 35 mM KCl; 4 mM DTT; 1 mM EDTA; 1.3% Triton X-100. 50 $\mu$l samples were taken to the reverse transcriptase activity tests and analyzed in a 100 $\mu$l reaction mixture containing 75 mM Tris-HCl, pH 8.0; 60 mM KCl; 6.2 mM $MgCl_2$; 6 mM DTT; 0.5 mM EDTA; 0.65% Triton X-100, 100 $\mu$g/ml BSA; 25 $\mu$Ci/ml $^3$H-dTTP (spec activity 80 Ci/mmol); 2.5 $\mu$g/ml $(dT)_{12-18}$; and 2.0 $\mu$g/ml $(rA)_n$. Incubation was for 1 hour at 37° C. and the TCA-insoluble product precipitated onto Whatman GF/A filter papers, washed and dried, and counted in a liquid scintillation counter. The test result is shown in Table III.

The amounts of reverse transcriptase molecules and their total activity expressed in HIV-infected cell cultures is correlated to the amount of HIV particles present. The addition of an effective antiviral agent which inhibits the production of new HIV particles, also decreases the amount of reverse transcriptase molecules and is expressed as a decreased total activity.

TABLE III

Effect of 3'-deoxy-3'-fluorothymidine on the expressed reverse transcriptase activity in HIV (HTLV-III/LAV)-infected H9 cells.

| Days post-infection | Reverse transcriptase activity (cpm × $10^{-3}$) in the presence of indicated amounts ($\mu$M) of 3'-deoxy-3'-fluorothymidine | | | | | |
|---|---|---|---|---|---|---|
| | 0 | 0.01 | 0.05 | 0.1 | 0.5 | 1.0 |
| 4 | 0.9 | 0.5 | 0.3 | 0.2 | 0.3 | 0.3 |
| 8 | 19 | 1.3 | 0.3 | 0.2 | 0.3 | 0.2 |
| 11 | 17 | 1.9 | 0.4 | 0.5 | 0.5 | 0.5 |
| 15 | 11 | 2.7 | 0.6 | 0.4 | 0.3 | 0.4 |
| 18 | 27 | 28 | 0.5 | 0.4 | 0.6 | 0.5 |
| 22 | 46 | 52 | 1.6 | 0.2 | 0.1 | 0.1 |
| 29 | 16 | 21 | 3.1 | 0.2 | 0.2 | 0.2 |

In table III is shown the effects of different concentrations of 3'-deoxy-3'-fluorothymidine on the reverse transcriptase activity of HIV (HTLV-III/LAV) during an incubation period of several weeks. The presence of 3'-deoxy-3'-fluorothymidine at 0.1 $\mu$M and higher concentrations completely prevents the enzyme activity during at least 29 days. At 0.05 $\mu$M of 3'-deoxy-3'-fluorothymidine no significant enzyme activity was detected up to 22 days and at 0.01 $\mu$M concentration, enzyme activity was not detected up to 11 days.

What is claimed is:

1. A method for therapeutic treatment of human immunodeficiency virus (HIV) infections in man, comprising administering an effective dose of a compound of the formula

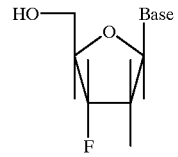

wherein Base is selected from the group consisting of thymine, cytosine, adenine and guanine, or a physiologically acceptable salt thereof to a man in need of such treatment.

2. A method for a therapeutic treatment of acquired immune deficiency syndrome (AIDS) in man, comprising administering an effective dose of a compound of the formula

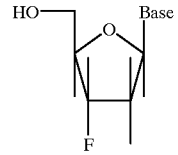

wherein Base is selected from the group consisting of thymine, cytosine, adenine and guanine, or a physiologically acceptable salt thereof to a man in need of such treatment.

3. A method for the therapeutic treatment of human T-cell lymphotropic virus infections in man, said virus being selected from the group consisting of HTLV-I and HTLV-II, comprising administering an effective dose of a compound of the formula

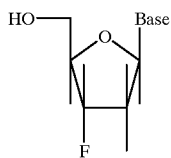

wherein Base is selected from the group consisting of thymine, cytosine, adenine and guanine, or a physiologically acceptable salt thereof to a man in need of such treatment.

4. A method for therapeutic treatment of acquired immunodeficiency syndrome (AIDS) in animals, comprising administering an effective dose of a compound of the formula

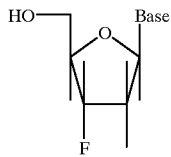

wherein Base is selected from the group consisting of thymine, cytosine, adenine and guanine, or a physiologically acceptable salt thereof to an animal in need of such treatment.

5. The method according to any one of claims 1, 2, 3 and 4 comprising administering 3'-deoxy-3'-fluorothymidine or a physiologically acceptable salt thereof.

6. The method according to any one of claims 1, 2, 3 and 4 comprising oral administration.

7. The method according to any one of claims 1, 2, 3 and 4 comprising intravenous administration.

8. The method according to any one of claims 1, 2, 3 and 4 comprising parenteral administration.

9. Method for treating a human infected by human immunodeficiency virus comprising administering to said infected human an anti-human immunodeficiency virus effective amount of a compound selected from the group consisting of 3'-fluoro-3'-deoxythymidine and 3'-fluoro-2',3'-dideoxyguanosine.

10. The method of claim 9, wherein said compound is 3'-fluoro-3'-deoxythymidine.

11. The method of claim 9, wherein said compound is 3'-fluoro-2',3'-dideoxyguanosine.

12. Method for protecting cells against HIV pathogenesis comprising administering to a human with HIV pathogenesis an amount of a compound selected from the group consisting of 3'-fluoro-3'-deoxythymidine and 3'-fluoro-2',3'-dideoxyguanosine effective to protect cells of said human against HIV pathogenesis.

13. A method for the treatment of AIDS, which comprises administering to a patient in need thereof a pharmaceutical composition comprising a therapeutically effective amount of a compound having the formula:

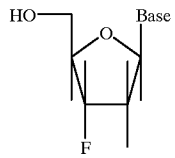

wherein the Base is adenine, cytosine, guanine, or thymine or a physiologically acceptable salt thereof, and a pharmaceutically acceptable carrier.

14. The method of claim 13, wherein said compound is one or more of 2',3'-dideoxy-3'-fluorothymidine and 2',3'-dideoxy-3'-fluorocytidine.

15. The method of claim 13, wherein the composition is in a unit dosage form suitable for administration by injection, oral ingestion or rectal application.

16. The method of claim 13, wherein the composition is in a dosage form of a tablet, capsule or granulate in the form of a unit dose.

17. The method according to claim 1, wherein B is guanine.

18. The method according to claim 2, wherein B is guanine.

19. The method according to claim 3, wherein B is guanine.

20. The method according to claim 4, wherein B is guanine.

21. The method according to claim 13, wherein B is guanine.

* * * * *